United States Patent [19]

Demerson et al.

[11] 4,355,031
[45] Oct. 19, 1982

[54] 2,3-DIHYDRO-3-[4-(SUBSTITUTED)-1-PIPERAZINYL]-1H-ISOINDOL-1-ONES

[75] Inventors: Christopher A. Demerson; Ivo L. Jirkovsky, both of Montreal, Canada

[73] Assignee: American Home Products Corp., New York, N.Y.

[21] Appl. No.: 262,717

[22] Filed: May 11, 1981

[51] Int. Cl.³ .............. C07D 403/04; C07D 403/14; A61K 31/41
[52] U.S. Cl. .................. 424/250; 544/360; 544/373; 544/295; 544/357; 260/326.11 R; 424/251; 544/364
[58] Field of Search .............. 544/360, 373, 364; 424/250

[56] References Cited

U.S. PATENT DOCUMENTS 3,579,524 5/1971 Van Dyke et al. .............. 544/373

FOREIGN PATENT DOCUMENTS 374068 2/1964 Switzerland .

OTHER PUBLICATIONS

Graf, W., et al., Helv. Chem. Acta, 42, pp. 1085–1101, 1959.
Topliss, J. G. et al., J. Med. Chem., 7, pp. 453–456, 1964.
P. Truitt et al., J. Med. Chem., 8,731 (1965).
H.-J. W. Vollmann et al., Chem. Berg., 105, 2933 (1972), see also Chem. Abstr., 77,151795d (1972), attached hereto.
R. R. Schmidt and E. Schlipp, Chem. Ber., 103, 3783 (1970), see also Chem. Abstr., 103, 3783 (1970), attached hereto.

Primary Examiner—Donald G. Daus
Assistant Examiner—Sharon A. Gibson
Attorney, Agent, or Firm—Arthur E. Wilfond

[57] ABSTRACT

Pyrazinoisoindolone derivatives of the formula

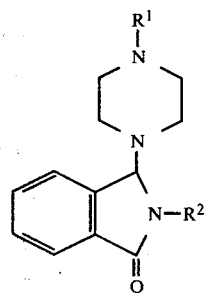

wherein $R^1$ is lower alkyl, phenyl, diphenylmethyl, pyridinyl, pyrimidinyl, pyrazinyl or pyrazinyl substituted with a lower alkyl, lower alkoxy or halo; and $R^2$ is hydrogen, lower alkyl or di(lower)alkylamino(lower)alkyl are useful as antihypertensive agents.

16 Claims, No Drawings

2,3-DIHYDRO-3-[4-(SUBSTITUTED)-1-PIPERAZINYL]-1H-ISOINDOL-1-ONES

This invention relates to novel pyrazinoisoindolone derivatives, to therapeutically acceptable salts thereof, to a process for their preparation, to pharmaceutical compositions thereof and to a method of using the derivatives. More specifically, the invention relates to 3-(1-piperazinyl)-1H-isoindol-1-one derivatives. The derivatives are useful for treating hypertension in mammals.

BACKGROUND OF THE INVENTION

Swiss Pat. No. 374,068, published Feb. 14, 1964 (see Farmdoc 11,020); P. Truitt, L. R. Brammer and L. T. Creagh, J. Med. Chem., 8, 731(1965); and Chem. Abstr., 77, 151795d (1972) for H.-J. W. Vollmann, K. Bredereck and H. Bredereck, Chem. Ber., 105, 2933 (1972) disclose 3-(1-piperazinyl)-1H-isoindol-1-one derivatives. The latter derivatives are distinguished readily from the compounds of the present invention by having different substituents, two of which are at position 3 of the 1H-isoindol-1-one nucleus. The present compounds have only one substituent at that position. Chem. Abstr., 74, 64158t (1971) for R. R. Schmidt and E. Schlipf, Chem. Ber., 103, 3783 (1970) discloses 1H-isoindol-1-one derivatives bearing a single substituent at position 3. The latter compounds, which were prepared in the course of a chemical investigation, differ from the compounds of the present invention in that they lack the pyrazino substituent on the 1H-isoindol-1-one nucleus.

SUMMARY OF THE INVENTION

The compounds of this invention are represented by formula I

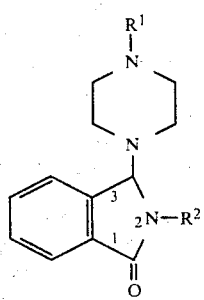

wherein $R^1$ is lower alkyl, phenyl, diphenylmethyl, pyridinyl, pyrimidinyl, pyrazinyl or pyrazinyl substituted with a lower alkyl, lower alkoxy or halo; and $R^2$ is hydrogen, lower alkyl or di(lower)alkylamino(lower)alkyl; or a therapeutically acceptable acid addition salt thereof.

A preferred group of compounds of this invention is represented by formula I wherein $R^1$ is lower alkyl, phenyl, diphenylmethyl, 2-pyridinyl, 4-pyridinyl, 2-pyrimidinyl, 2-pyrazinyl or 5-halo-2-pyrazinyl; and $R^2$ is as defined hereinabove; or a therapeutically acceptable acid addition salt thereof.

Another preferred group of compounds of this invention is represented by formula I wherein $R^1$ is methyl, phenyl, diphenylmethyl, 2-pyridinyl, 4-pyridinyl, 2-pyridimidinyl, 2-pyrazinyl or 5-chloro-2-pyrazinyl; and $R^2$ is methyl, ethyl, 1-methylethyl, (N,N-dimethylamino)ethyl or (N,N-dimethylamino)-propyl; or a therapeutically acceptable acid addition salt thereof.

A most preferred group of compounds of this invention is represented by formula I wherein $R^1$ is 2-pyridyl or 4-pyridyl and $R^2$ is lower alkyl or di(lower)alkylamino(lower)alkyl, or a therapeutically acceptable acid addition salt thereof.

The compounds of formula I can be prepared by a process described hereinafter.

A pharmaceutical composition is provided by combining the compound of formula I, or a therapeutically acceptable acid addition salt thereof, and a pharmaceutically acceptable carrier.

The compounds of this invention can be used to treat hypertension in a hypertensive mammal by administering to the mammal a effective anti-hypertensive amount of a compound of formula I or a therapeutically acceptable acid addition salt thereof.

DETAILED DESCRIPTION OF THE INVENTION

The term "lower alkyl" as used herein means a straight chain alkyl radical containing from one to six carbon atoms or a branched chain alkyl radical containing from three to four carbon atoms and includes methyl, ethyl, propyl, 1-methylethyl, butyl, 1,1-dimethylethyl, pentyl and hexyl. Preferred lower alkyl radicals contain one to three carbon atoms.

The term "lower alkoxy" as used herein means a straight chain alkoxy radical containing from one to six carbon atoms preferably one to three carbon atoms, or a branched chain alkoxy radical containing three or four carbon atoms, and includes methoxy, ethoxy, 1-methylethoxy, butoxy and hexanoxy.

The term "lower alkanol" as used herein means both straight and branched alkanols containing from one to four carbon atoms and includes methanol, ethanol, 1-methylethanol and butanol.

The term "organic proton acceptor" as used herein means the organic bases or amines, for instance, triethylamine, pyridine, N-ethylmorpholine and 1,5-diazabicyclo[4.3.0]non-5-ene.

The term "inorganic proton acceptor" as used herein means the inorganic bases, preferably the alkali metal hydrides, hydroxides, carbonates and bicarbonates, for example, sodium hydride, sodium hydroxide, potassium hydroxide, sodium carbonate, sodium bicarbonate or potassium carbonate.

The term "proton acceptor" as used herein means a proton acceptor selected from an organic proton acceptor and inorganic proton acceptor, as defined hereinabove.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or a therapeutically acceptable acid addition salt thereof is demonstrated in standard pharmacological tests, for example, in tests conducted in the spontaneously hypertensive rat (SHR) such as described by I. Varva, et al., Can. J. Physiol. Pharmacol., 51, 727(1973). The latter test method is modified in the following manner: Male rats, Okamota-Aoki Strain, ranging in weight between 250–400 g were anesthetized with diethyl ether. Their left femoral arteries and veins were cannulated with polyethylene tubing of the appropriate size. Each animal was then enfolded in a rubber mesh jacket which was secured with four towel clamps. The animal was suspended via the towel clamps from a bar and allowed to recover from the anesthesia. The femorial arterial cannula was connected to a Stratham pressure transducer (Model P23, Gould Stratham Instruments, Hato Rey, Porto Rico), which in turn was attached to a polygraph for recording arterial pressure and pulse rate. The pulse rate was considered to be the heart rate.

When the blood pressure (BP) had stabilized (usually two hours after cessation of the anesthesia) the intravenous injection of the standard agonists was begun. Each of the four agonists was prepared from concentrated, refrigerated, stock solutions to be delivered in a volume of 1 ml/kg. The doses given were: isoproterenol 0.5 $\mu$g/kg, adrenalin 2.0 $\mu$g/kg, tyramine 200 $\mu$g/kg and angiotensin I 0.25 $\mu$g/kg. The agonists were usually given in random order except that tyramine was never preceded by isoproterenol as the response to tyramine seemed to be blunted after a prior injection of isoproterenol. Enough time was allowed for the BP to return to preinjection levels before the next agonist was given. After the last agonist was given the test compound was administered by gastric gavage in a volume of 5 ml/kg. Heart rate and blood pressure were noted at 5, 10, 15, 30, 45 and 60 minutes and hourly thereafter for a period of at least four hours after drug administration. At one and two hours post-drug, the agonists were again injected at the same concentration and in the same order as during the control period.

Using this method, the following representative compounds of formula I were effective for reducing the blood pressure (BP) in the spontaneously hypertenstive rat (the amount of test compound and the percentage reduction in PB caused by that amount are indicated in the parentheses): 2,3-dihydro-3-[4-(2-pyrimidinyl)-1-piperazinyl]-1H-isoindol-1-one (described in example 2, at a dose of 50 mg/kg of body weight caused a 14% decrease in mean BP at two hours), 2,3-dihydro-3-[4-(4-pyridinyl)-1-piperazinyl]-1H-isoindol-1-one dihydrochloride (described in example 2, at a dose of 25 mg/kg of body weight caused a 16% decrease in mean BP at one hour), 2,3-dihydro-3-(4-phenyl-1-piperazinyl)-1H-isoindol-1-one (described in example 3, at a dose of 50 mg/kg of body weight caused an 8% decrease in mean BP at three hours), 2,3-dihydro-2-ethyl-3-[4-(2-pyridinyl)-1-piperazinyl]-1H-isoindol-1-one hydrochloride (described in example 4, at a dose of 50 mg/kg of body weight caused a 41% decrease in mean BP at four hours), 2,3-dihydro-2-(1methylethyl)-3-[4-(2-pyridinyl)-1-piperazinyl]-1H-isoindol-1-one (described in example 4, at a dose of 5 mg/kg of body weight caused a 17% decrease in BP at two hours), 2,3-dihydro-2-[(N,N-dimethylamino)propyl]-3-[4-(2-pyridinyl)-1-piperazinyl]-1H-isoindol-1-one (described in example 4, at a dose of 50 mg/kg of body weight caused a 34% decrease in mean BP at four hours), 2,3-dihydro-2-[(N,N-dimethylamino)ethyl]-3-[4-(2-pyridinyl)-1-piperazinyl]-1H-isoindol-1-one (described in example 4, at a dose of 50 mg/kg of body weight caused a 21% decrease in mean BP at four hours), and 2,3-dihydro-2-methyl-3-[4-(2-pyridinyl)-1-piperazinyl]-1H-isoindol-1-one (described in example 5, at a dose of 5 mg/kg of body weight caused a 17% decrease in mean BP at two hours).

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects.

For example, the effective antihypertensive amount of the compounds for oral administration usually ranges from about 0.1 to 200 mg per kilogram body weight per day in single or divided doses although as aforementioned variations will occur. However, a dosage level that is in the range of from about 1.0 to 100 mg per kilogram body weight per day in single or divided doses is employed most desirably for oral administration in order to achieve effective results.

The compound of formula I also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such diuretic and/or antihypertensive therapeutic agents include, for example, the thiazide diuretics for instance, chlorothiazide or hydrochlorothiazide; mineralocorticoid antagonizing diuretic agents, e.g., spironolactone; and other diuretics such as triamterene and furosemide. Examples of still other suitable antihypertensive agents are prazosine, hydralazine and centrally active antihypertensive agents such as methyldopa, clonidine, and reserpine; as well as the β-adrenergic blocking agents, for instance, propranolol. The compound of formula I can be administered sequentially or simultaneously with the antihypertensive and/or diuretic agent. Preferred antihypertensive and/or diuretic therapeutic agents are the antihypertensive agents such as the thiazides, mineralocorticoid antagonizing diuretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physician Desk Reference", 34 ed., Medical Economics Co., Oradell, N.J., U.S.A., 1980. For example, the agent propranolol is administered daily to humans in a range of 80 to 640 mg, usually in the form of unit doses of 10, 20, 40 or 80 mg. When used in combination the compound of formula I is administered as described previously.

Process

The compounds of formula I in which $R^1$ is as defined herein and $R^2$ is hydrogen can be prepared by a process illustrated as follows:

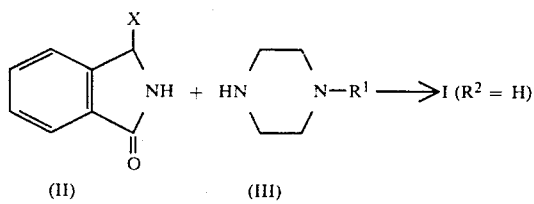

wherein X is bromo or chloro and $R^1$ is as defined herein.

The starting materials of formula II or III are either known or can be prepared by known methods. A convenient starting material of formula III is 3-chlorophthalimidine, described by R. R. Schmidt and E. Schlipf, Chem. Ber., 103, 3783(1970). The preparation of a number of the starting materials of formula III is illustrated by examples 1 and 1a 1d, described hereinafter.

More generally, the compounds of formula I in which $R^1$ and $R^2$ are as defined herein can be prepared by a process comprising:

(a) condensing the compound of formula II in which X is bromo or chloro with a compound of formula III in which $R^1$ is as defined herein to obtain the compound of formula I in which $R^1$ is as defined herein and $R^2$ is hydrogen; and (b) when the compound of formula I in which $R^1$ is as defined herein and $R^2$ is lower alkyl or di(lower)alkylamino(lower)alkyl is required, N-alkylating the compound of formula I in which $R^1$ is as defined herein and $R^2$ is hydrogen in the presence of a proton acceptor with a compound of formula $R^2$-Y in which $R^2$ is lower alkyl or di(lower)alkylamino(lower)alkyl and Y is bromo, chloro or iodo; and, if desired, converting the compound of formula I into its corresponding therapeutically acceptable acid addition salt.

More specifically, practical and convenient conditions for condensing the compound of formula Ii in which X is bromo or chloro with the compound of formula III in which $R^1$ is as defined herein include bringing the two reactants in contact with each other in an inert organic solvent at temperatures ranging from 0° to 60° C. from 30 minutes to six hours. Suitable solvents include acetonitrile, dimethylformamide, diethyl ether, benzene or tetrahydrofuran. Acetonitrile is a preferred solvent.

Thereafter, if a compound of formula I in which $R^1$ is as defined herein and $R^2$ is lower alkyl or di(lower)alkylamino(lower)alkyl is required, the last named compound of formula I in which $R^2$ is hydrogen is subjected to N-alkylation with the compound of formula $R^2$-Y in which $R^2$ is lower alkyl or di(lower)alkylamino(lower)alkyl and Y is bromo, chloro or iodo.

Practical and convenient conditions for effecting the N-alkylation include the use of one to two molar equivalents of the proton acceptor. Inorganic proton acceptors, for example, sodium hydride, sodium hydroxide or potassium carbonate, have been found to be suitable proton acceptors. Any solvent, which does not interfer with the reaction, can serve as the reaction medium. Suitable solvents include dimethylformamide, dimethylsulfoxide, toluene, acetone and tetrahydrofuran. Preferred conditions for effecting the N-alkylation include the use of sodium hydride as the proton acceptor and dimethylformamide as the solvent. Although the optimum temperature and reaction time will vary depending on the reactants employed, the reaction is performed generally at 50° to 100° C., or the boiling point of the reaction mixture, for a period of 30 minutes to 48 hours.

The following examples illustrate further this invention.

EXAMPLE 1

N-Pyrimidinylpiperazine

A mixture of piperazine (22.5 g, 0.26 mole), potassium iodide (14.5 g, 0.087 mol), sodium carbonate (43.6 g, 0.44 mol) and 2-chloropyrimidine (10.0 g, 0.087 mol) in 50 ml of toluene was heated at reflux for 18 hr. The reaction mixture was filtered. Evaporation of the filtrate gave a semi-solid (16.3 g). The semi-solid was subjected to chromatography on silica gel using 30% methanol in chloroform as the eluant. Pooling of the appropriate fractions gave 9.1 g of the title compound, NMR (CDCl$_3$) δ1.8(s, 1H), 2.9 (t,J=5 Hz, 4 H), 3.75 (t,J=5 Hz, 4H), 6.4 (t,J=5 Hz,1H), 8.25 (d,J=5, 2 Hz).

EXAMPLE 1a 1-(5-Chloro-2-pyrazinyl)piperazine

A mixture of 2,5-dichloropyrazine (14.9 g, 0.1 mol), piperazine (50.5 g, 0.59 mol), acetone (22.5 ml), water (20 ml) and concentrated aqueous HCl (1.8 ml) was heated at reflux for 3 hr. The reaction mixture was cooled, diluted with water, filtered and the acetone was removed by distillation. The aqueous solution was then extracted thrice with chloroform. The combined extracts were washed twice with water, dried (Na$_2$SO$_4$) and evaporated to dryness to afford 7.3 g of solid, m.p. 98°–102°. J. K. Boissier et al., J. Med. Chem., 6, 541 (1963) report a m.p. of 101° C.

EXMPLE 1b 1-(2-Pyrazinyl)piperazine

A mixture of 2-chloropyrazine (15.0 g, 0.13 mol), piperazine (66.1 g, 0.77 mol), acetone (33 ml), water (30 ml) and concentrated aqueous HCl (24 ml) was heated at reflux for 3 hrs. The mixture was cooled, filtered and most of the acetone was removed by distillation. Water was added to the residual mixture. The mixture was extracted with chloroform (4x). The combined chloroform extract was washed with water (3x), dried (Na$_2$SO$_4$) and evaporated to dryness to give 21 g of oil. The oil was subjected to chromatography on silica gel using 20% methanol in chloroform as the eluant. Pooling of the appropriate fractions afforded 8.86 g of the title compound, NMR(CDCl$_3$)δ1.9 (s,1H), 2.95 (m, 4H), 3.5 (m, 4H), 7.75 (m,1H), 8.0 (m, 2H).

EXAMPLE 1c 1-(4-Pyridinyl)piperazine

A mixture of piperazine (67.0 g, 0.78 mol) and 4-chloropyridine (26.1 g, 0.23 mol) in xylene (520 ml) was heated at reflux for 20hr. The reaction mixture was cooled and filtered. The filtrate was evaporated to dryness to give 5.96 g of the title compound as a solid; m.p. 132°–136° C.; NMR(CDCl$_3$) δ1.8(s,1H), 2.9(m,4H), 3.2(m,4H), 6.6(m,2H), 8.2(m,2H).

EXAMPLE 1d

N-(Diphenylmethyl)piperazine

A stirred mixture of diphenylmethyl bromide (40 g, 0.16 mol), piperazine (27.8 g, 0.32 mol), potassium iodide (26.8 g, 0.16 mol) and sodium carbonate (86 g, 0.81 mol) in toluene (400 ml) was heated at reflux for 3.5 hr. The reaction mixture was filtered. The filtrate was evaporated to dryness to give 40 g of crude product. The crude product was purified by chromatography using 10% methanol in chloroform as the eluant. Pooling of the appropriate fractions gave 4.5 g of the title compound, NMR (CDCl$_3$) δ1.82 (s,1H), 2.3(t,J=5 Hz,4H), 2.85 (t,J=5 Hz, 4H), 4.2 (s,1H), 7.3 (m,10H).

EXAMPLE 2

2,3-Dihydro-3(4-methyl-1-piperazinyl)-1H-isoindol-1-one (I,R$^1$=CH$_3$ and R$^2$=H)

A mixture of the compound of formula II, 3-chlorophthalimidine [10.0 g, 0.06 mol, described by R. R. Schmidt and E. Schlipf, Chem. Ber., 103, 3783 (1970)], and the compound of formula III, N-methylpiperazine (17.8 g, 0.178 mole) in acetonitrile (200 ml) was stirred at 22° C. for 2 hr. The resulting precipitate was collected, washed with a small amount of cold water and dried. The precipitate was purified by chromatography on silica gel using 15% methanol in chloroform as eluant. The appropriate fractions were pooled to afford 8.2 g of the title compound. The title compound was converted to its corresponding dihydrochloride salt with a solution of hydrogen chloride in ethanol. The dihydrochloride salt had m.p. 168°–170° C., NMR(DMSO-d$_6$) δ2.75(s, 3H), 3.2(m, 8H), 5.7(s,1H), 5.7(s,2H), 9.17(s,1H); Anal Calcd for C$_{13}$H$_{17}$N$_3$O$_2$ HCl: C, 51.32% H, 6.29% N, 13.81%; Found: C, 50.11% H, 6.78%, N, 13.77%.

By following the procedure of Example 2, but replacing the compound of formula III with an equivalent amount of N-pyrimidinylpiperazine, described in Example 1, 2,3-dihydro-3-[4-(2-pyrimidinyl)-1-piperazinyl]-1H-isoindol-1-one; m.p. 252°–255° C.; NMR (CDCl$_3$) δ2.57(m, 4H), 3.8(t,J =5 Hz, 4H), 5.45(s,1H), 6.42(t,J=5 Hz, 1H), 7.53 (m, 3H), 7.78(m), 8.27 (d,J=5 Hz,2H); IR(CHCl$_3$) 3430, 3200, 1694, 1581 cm$^{-1}$; Anal Calcd for C$_{16}$H$_{17}$N$_5$O: C, 65.06% H, 5.80% N, 23.72%; Found: C, 64.98% H, 5.84% N, 23.74%, was obtained.

Likewise, replacement of the compound of formula III with 1-(5-chloro-2-pyrazinyl)piperazine, described in example 1a, gave 2,3-dihydro-3-[4-(5-chloro-2-pyrazinyl)-1-piperazinyl]-1H-isoindol-1-one; m.p. 263°–266° C.; NMR (DMSO-d$_6$) δ2.5(m, 4H), 3.57 (t,J=5Hz, 4H), 5.50 (s,1H), 7.5(m, 4H), 8.75 (s, 1H); IR(Nujol) 3200, 1697, 1660 cm$^{-1}$; Anal Calcd for C$_{16}$H$_{16}$-ClN$_5$O: C, 58.27% H, 4.89% N, 21.24%; Found: C, 58.38% H, 4.97% N, 21.31%.

Likewise, replacement of the compound of formula III with 1-(2-pyrazinyl)piperazine, described in example 1b, gave 2,3-dihydro-3-[4-(2-pyrazinyl)-1-piperazinyl]-1H-isoindol-1-one; m.p. 242°–246° C.; NMR(DMSO-d$_6$) δ2.5 (m, 4H), 3.55 (m, 4H), 5.5 (s,1H), 7.8(m, 7H),8.8 (s, 1H); IR (Nujol*) 3170, 3070, 1707 cm$^{-1}$; Anal Calcd for C$_{16}$H$_{17}$N$_5$O: C, 65.06%, H, 5.80% N, 23.72%; Found: C, 65.01% H, 5.81% N, 23.76%.

* Trademark for a brand of white mineral oil

Likewise, replacement of the compound of formula III with 1-(4-pyridinyl)piperazine described in example 1c, gave 2,3-dihydro-3-[4-(4-pyridinyl)-1-piperazinyl]-1H-isoindol-1-one, m.p. 210°–214° C. The dihydrochloride salt of the latter compound had m.p. 354°–358° C.; NMR (CDCl$_3$) δ2.4-3.4 (m, 8H), 5.45(s, 1H), 7.4 (m, 8H); IR (CHCl$_3$) 3410, 3060, 2520, 1730 cm$^{-1}$; Anal Calcd for C$_{17}$H$_{18}$N$_4$O.2 HCl: C, 69.36% H, 6.16% N, 19.04%; Found: C,68.73% H, 6.20% N, 18.69%.

EXAMPLE 3

2.3-Dihydro-3[4-(diphenylmethyl)-1-piperazinyl]-1H-isoindol-1-one (R$^1$=diphenylmethyl and R$^2$=H)

A mixture of the compound of formula II, 3-chlorophthalimidine (10.8 g, 0.064) mol) and the compound of formula III, N-(diphenylmethyl)-piperazine (24.5 g, 0.097 mol, described in example 1d), in acetonitrile (320 ml) was stirred at 22° C. for 3 hr. The resulting precipitate was collected, washed with a small amount of acetonitrile and recrystallized from ethanol to afford the title compound, m.p. 225°–229° C.

The dihydrochloride salt of the title compound has m.p. 182°–184° C.; NMR (DMSO-d$_6$) δ3.15 (m, 8H), 5.6 (s, 1H), 5.65 (s, 1H), 6.15 (broad multiplet, 2H), 7.6(m, 14H), 9.1(s, 1H); Anal Calcd for C$_{25}$H$_{25}$N$_3$O.2 HCl: C, 78.23% H, 6.57% N, 10.96%; Found: C, 77.99% H, 6.77% N, 10.97%.

By following the procedure of example 3, but replacing the compound of formula III with an equivalent amount of 1-(2-pyridinyl)-piperazine, 2,3-dihydro-3-[4-(2-pyridinyl)-1-piperazinyl]-1H-isoindol-1-one, m.p. 251°-255° C., was obtained. The dihydrochloride salt of the latter compound had m.p. 198°-200° C.; NMR (DMSO-d$_6$) δ3.05(m, 4H), 4.05 (m, 4H), 6.05 (s, 1H), 7.65 (m, 8H), 9.3 (s, 1H), 9.8 (broad multiplet, 2H); Anal Calcd for C$_{17}$H$_{18}$N$_4$O.2 HCl: C, 69.36% H, 6.16% N, 19.04%; Found: C, 69.18% H, 6.23% N, 18.90%.

Likewise, replacement of the compound of formula III with N-phenylpiperazine gave 2,3-dihydro-3-(4-phenyl-1-piperazinyl)-1H-isoindol-1-one; m.p. 234°-237° C.; NMR (DMSO-d$_6$) δ2.6(t,J=5 Hz, 4), 3.1 (t, J=5 Hz, 4H), 5.45 (s, 1H), 6.95 (m, 4H), 7.55 (m, 5H), 8.8 (s, 1H); IR (CHCl$_3$) 3200, 1695, 1660 cm$^{-1}$; Anal Calcd for C$_{18}$H$_{19}$N$_3$O: C, 73.69% H, 6.52% N, 14.32%; Found: C, 73.72% H, 6.60% N, 14.27%.

EXAMPLE 4

2,3-Dihydro-2-(1-methylethyl)-3-[4-(2-pyridinyl)-1-piperazinyl]-1H-isoindol-1-one (R$^1$=2-pyridinyl and R$^2$=CH(CH$_3$)$_2$)

A solution of 2,3-dihydro-3-[4-(2-pyridinyl)-1-piperazinyl]-1H-isoindol-1-one (12.0 g, 0.04 mol, described in example 3) in N,N-dimethylformamide (170 ml) was added to a stirred suspension of sodium hydride (2.9 g, 0.06 mol, 50% dispersion in oil) in dimethylformamide (200 ml). After raising the temperature of the mixture to 90°-100° C., a solution of 2-iodopropane (13.86 g, 0.08 mol) in 100 ml of dimethylformamide was added dropwise to the mixture. The reaction mixture was stirred at 90°-100° C. for 24 hr, cooled, diluted with water and extracted with diethyl ether (4x). The combined extracts were washed with water, dried (Na$_2$SO$_4$) and evaporated to dryness to give 8.29 g of a solid. The solid was purified by chromatography on silica gel using 20% acetone in toluene as the eluant. Pooling of the appropriate fractions gave 3.18 g of the pure title compound. After recrystallization from hexane, the title compound had m.p. 118°-123° C.; NMR (CDCl$_3$) δ1.45 & 1.5 (d, J=7 Hz, 6), 2.7 (m, 4H), 3.55 (m, 4H), 4.35 (octet, J=7 Hz, 1H), 5.3 (s, 1H), 7.4 (m, 8H); IR (CHCl$_3$) 1685 cm$^{-1}$; Anal Calcd for C$_{20}$H$_{24}$N$_4$O: C, 71.40% H, 7.19% N, 16.65%: Found: C, 71.22% H, 7.29% N, 16.36%.

By following the procedure of example 4 but replacing 2-iodopropane with an equivalent amount of 3-dimethylaminopropyl iodide, 2,3-dihyro-2-[(N,N-dimethylamino)propyl]-3-[4-(2-pyridinyl)-1-piperazinyl]-1H-isoindol-1-one; m.p. 74°-79° C.; NMR (CDCl$_3$) δ1.9 (m, 2H), 2.2 (s, 6H), 2.6 (m, 6H), 3.7 (m, 6H), 5.3 (s, 1H), 6.3 (m, 1H), 7.7 (m, 7H); IR (CHCl$_3$) 1677 cm$^{-1}$; Anal Calcd for C$_{22}$H$_{29}$N$_5$O: C, 69.62% H, 7.70% N, 18.47%; Found: 69.92%, H, 8.02% N, 17.89%; was obtained.

Likewise, replacement of the 2-iodopropane with 2-dimethylaminoethyl chloride gave 2,3-dihydro-2[(N,N-dimethylamino)ethyl]-3-[4-(2-pyridinyl)-1-piperazinyl]-1H-isoindol-1-one. The maleate salt of the latter compound, after recrystallization from methanol-diethyl ether, had m.p. 197°-199° C.; NMR (DMSO-d$_6$) δ2.85 (s, 6H), 3.5 (m, 10H), 5.55 (s, 1H), 6.0 (m, 2H), 7.4 (m, 8H); IR (Nujol* ) 2500, 1685 cm$^{-1}$; Anal Calcd for C$_{21}$H$_{25}$N$_5$O.C$_4$H$_4$O$_4$: C, 62.35% H,6.49% N, 14.54%; Found: C, 62.23% H, 6.51% N, 14.42%.

* Trademark

Likewise replacement of the 2-iodopropane with iodoethane gave 2,3-dihydro-2-ethyl-3-[4-(2-pyridinyl)-1-piperazinyl]-1H-isoindol-1-one. The hydrochloride salt of the latter compound, after recrystallization from ethanol-diethyl ether, had m.p. 126°-128° C.; NMR (DMSO-d$_6$) δ2.85 (s, 6H), 3.5 (m, 10H), 5.55 (s, 1H) 6.0 (m, 2H), 7.4 (m, 8H); IR (Nujol* ) 2500, 1685 cm$^{-1}$.

EXAMPLE 5

2,3-Dihydro-2-methyl-3-[4-(2-pyridinyl)-1-piperazinyl]-1H-isoindol-1-one (I, R$^1$=2-pyridinyl and R$^2$=CH$_3$)

A solution of 2,3-dihydro-3-[4-(2-pyridinyl)-1-piperazinyl]-2H-isoindol-1-one (4.84 g, 0.016 mol, described in example 3) in dimethylformamide (100 ml) was added dropwise to a stirred suspension of sodium hydride (1.18 g, 0.025 mol, 50% dispersion in oil) in dimethylformamide (75 ml). After raising the temperature of the mixture to 90°-100° C., a solution of iodomethane (4.67 g, 0.33 mol) in dimethylformamide (40 ml) was added to the mixture. The reaction mixture was stirred at 90°-100° C. for 19 hr, cooled, diluted with water and extracted with diethyl ether (4x). The combined extracts were washed with water; dried (Na$_2$SO$_4$) and evaporated to dryness. The residual solid (2.35 g) was recrystallized from benzene-petroleum ether (30°-60° C.) to give 1.0 g of the title compound; m.p. 152°-155° C.; NMR (DMSO-d$_6$) δ2.6 (t, J=5, 4H), 3.0 (s, 3H), 3.43 (m, 4H), 5.35 (s, 1H), 7.5 (m, 8H), IR (Nujol *) 1680cm$^{-1}$; Anal Calcd for C$_{18}$H$_{20}$N$_4$O: C, 70.10% H, 6.54% N, 18.17%; Found: C, 69.91% H, 6.47% N, 17.93%.

*Trademark

We claim:

1. A compound of formula I

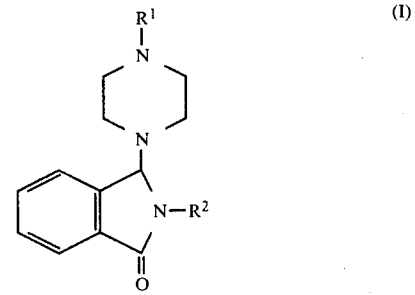

wherein R$^1$ is lower alkyl, phenyl, diphenylmethyl, or pyridinyl; and R$^2$ is hydrogen, lower alkyl or di(lower)alkylamino(lower) alkyl; or a therapeutically acceptable acid addition salt thereof.

2. The compound of claim 1 wherein R$^1$ is lower alkyl, phenyl, diphenylmethyl, 2-pyridinyl, 4-pyridinyl; or a therapeutically acceptable acid addition salt thereof.

3. The compound of claim 1 wherein R$^1$ is methyl, phenyl, diphenylmethyl, 2-pyridinyl, 4-pyridinyl; and R$^2$ is methyl, ethyl, 1-methylethyl, (N,N-dimethylamino)ethyl or (N,N-dimethylamino)propyl; or a therapeutically acceptable acid addition salt thereof.

4. The compound of claim 1 wherein R$^1$ is 2-pyridinyl or 4-pyridinyl and R$^2$ is lower alkyl or di(lower)alkylamino(lower)alkyl, or a therapeutically acceptable acid addition salt thereof.

5. 2,3-Dihydro-3-(4-methyl-1-piperazinyl)-1H-isoindol-1-one, as claimed in claim 1.

6. 2,3-Dihydro-3-[4-(4-pyridinyl)-1-piperazinyl]-1H-isoindol-1-one, as claimed in claim 1.

7. 2,3-Dihydro-3-[4-(diphenylmethyl)-1-piperazinyl]-1H-isoindol-1-one, as claimed in claim 1.

8. 2,3-Dihydro-3-[4-(2-pyridinyl)-1-piperazinyl]-1H-isoindol-1-one, as claimed in claim 1.

9. 2,3-Dihydro-3-(4-phenyl-1-piperazinyl)-1H-isoindol-1-one, as claimed in claim 1.

10. 2,3-Dihydro-2-(1-methylethyl)-3-[4-(2-pyridinyl)-1-piperazinyl]-1H-isoindol-1-one, as claimed in claim 1.

11. 2,3-Dihydro-2-[(N,N-dimethylamino)propyl]-3-[4-(2-pyridinyl)-1-piperazinyl]-1H-isoindol-1-one, as claimed in claim 1.

12. 2,3-Dihydro-2-[(N,N-dimethylamino)ethyl]-3-[4-(2-pyridinyl)-1-piperazinyl]-1H-isoindol-1-one, as claimed in claim 1.

13. 2,3-Dihydro-2-ethyl-3-[4-(2-pyridinyl)-1-piperazinyl]-1H-isoindol-1-one, as claimed in claim 1.

14. 2,3-Dihydro-2-methyl-3-[4-(2-pyridinyl)-1-piperazinyl]-1H-isoindol-1-one, as claimed in claim 1.

15. An antihypertensive pharmaceutical composition which comprises a compound of claim 1, or a therapeutically acceptable acid addition salt thereof, and a pharmaceutically acceptable carrier therefor.

16. A method of treating hypertension in a hypertensive mammal which comprises administering to said mammal an effective antihypertensive amount of a compound of claim 1 or a therapeutically acceptable acid addition salt thereof.

* * * * *